United States Patent [19]

Bru-Magniez et al.

[11] Patent Number: 5,200,408
[45] Date of Patent: Apr. 6, 1993

[54] ANALGESIC α-AMINO-N-PYRIDYLBENZENEPROPANAMIDE DERIVATIVES AND PHARMACEUTICAL COMPOSITIONS CONTAINING THEM

[75] Inventors: Nicole Bru-Magniez; Eric Sartori, both of Paris; Jean-Marie Teulon, La Celle Saint Cloud, all of France

[73] Assignee: Laboratoires UPSA, Agen, France

[21] Appl. No.: 849,709

[22] Filed: Mar. 11, 1992

[30] Foreign Application Priority Data

Feb. 11, 1992 [FR] France .................. 92 01521

[51] Int. Cl.$^5$ .................. C07D 213/36; A61K 31/44
[52] U.S. Cl. .................. 514/237.2; 514/332; 514/336; 514/255; 514/353; 544/124; 544/360; 544/365; 546/257; 546/283; 546/284; 546/306
[58] Field of Search .............. 546/309, 275, 194, 283, 546/284, 257, 306; 544/60, 124, 360, 365; 514/227.8, 237.2, 255, 318, 343, 353, 332, 336

[56] References Cited

PUBLICATIONS

Altman et al. *J. Med. Chem.* vol. 24, 1984, pp. 596-600, "Synthesis of Pyridine Derivates of L-Phenylalanine as Antisickling Reagents".

*Primary Examiner*—C. Warren Ivy
*Assistant Examiner*—Zinna N. Davis
*Attorney, Agent, or Firm*—Armstrong, Westerman, Hattori, McLeland & Naughton

[57] ABSTRACT

The present invention relates to the derivatives of the formula

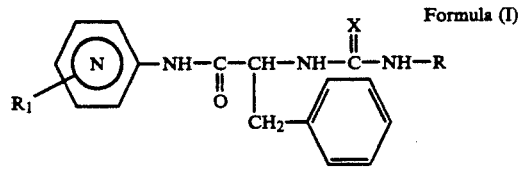

Formula (I)

in the (S) configuration, to their addition salts and to their use in therapy, especially as drugs with analgesic properties.

12 Claims, No Drawings

ANALGESIC α-AMINO-N-PYRIDYLBENZENEPROPANAMIDE DERIVATIVES AND PHARMACEUTICAL COMPOSITIONS CONTAINING THEM

The present invention relates, by way of novel products, to the α-amino-N-pyridylbenzenepropanamide derivatives of general formula (I) below and, if appropriate, to their addition salts, in particular the pharmaceutically acceptable addition salts.

The compounds in question have a very valuable pharmacological profile insofar as they possess analgesic properties. They will therefore be particularly indicated for the treatment of pain. There may be mentioned, for example, their use in the treatment of muscular, articular or nervous pains, dental pains, herpes zoster and migraines, in the treatment of rheumatic complaints and pains of cancerous origin, and also as complementary treatments for infectious and febrile states.

The present invention further relates to the method of preparing said products and to their applications in therapy.

These α-amino-N-pyridylbenzenepropanamide derivatives have general formula (I):

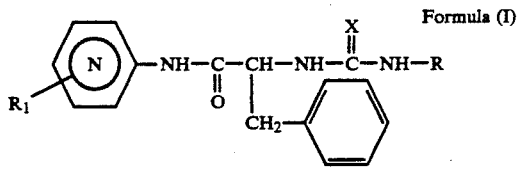

Formula (I)

in the (S) configuration, in which:

R can be a hydrogen atom or a group (CH—R$_4$)$_n$-A, R$_4$ being the hydrogen atom or an aromatic ring, n being an integer from 0 to 5 and A being a lower alkyl radical, a C$_3$–C$_7$ cycloalkyl radical or an aromatic or heteroaromatic ring; R can also be a group —(CH$_2$)$_n$—N(R$_2$R$_3$), in which n is as defined above and R$_2$ and R$_3$ are lower alkyl radicals or C$_3$–C$_7$ cycloalkyl radicals or form, together with the nitrogen atom to which they are attached, a ring such as pyrrolidine, piperidine, morpholine, thiomorpholine or piperazine N-substituted by a lower alkyl radical, a C$_3$–C$_7$ cycloalkyl radical or an aromatic or heteroaromatic ring;

the nitrogen atom of the pyridine ring can be in the 2-, 3- or 4-position of the amide group;

R$_1$ is a hydrogen atom, a halogen atom, a lower alkyl radical or a group COOR′, R′ being the hydrogen atom or a lower alkyl radical; and X is the oxygen atom or the sulfur atom.

In the description and the claims, lower alkyl radical is understood as meaning a linear or branched hydrocarbon chain having from 1 to 6 carbon atoms. A linear or branched lower alkyl radical is, for example, a methyl, ethyl, propyl, isopropyl, butyl, isobutyl, tert-butyl, pentyl, isopentyl, hexyl or isohexyl radical.

C$_3$–C$_7$ cycloalkyl radical is understood as meaning a saturated cyclic radical; it is preferably a cyclopropane, cyclobutane, cyclopentane, cyclohexane or cycloheptane radical.

Halogen is understood as meaning a chlorine, bromine, iodine or fluorine atom.

Aromatic ring is understood as meaning a phenyl group which is unsubstituted or substituted by a lower alkyl radical, one or two halogens, a trifluoromethyl, a nitro group, an amino group, an OH or O-lower alkyl group or an SH or S-lower alkyl group. An aromatic ring is for example a methylphenyl, monochloro- or dichloro-phenyl, trifluoromethylphenyl, nitrophenyl, aminophenyl or methoxyphenyl radical.

Heteroaromatic ring is understood as meaning an aromatic ring having from 5 to 7 atoms and containing at least one heteroatom selected from nitrogen, oxygen or sulfur, it being possible for this aromatic ring to be substituted by a lower alkyl radical, one or two halogens, a trifluoromethyl, a nitro group, an amino group, an OH or O-lower alkyl group or an SH or S-lower alkyl group. A heteroaromatic ring is for example a furanyl, pyrrolyl, thienyl, pyranyl, pyridyl, oxazolyl, thiazolyl, pyrazolyl, pyrazinyl, pyridazinyl or pyrimidinyl group.

According to one feature of the invention,

R is hydrogen, a phenylethyl radical, a group (CH$_2$)$_n$—A in which n is an integer from 0 to 5 and A is a radical selected from the group comprising a lower alkyl radical, a C$_3$–C$_7$ cycloalkyl radical, a phenyl group which is unsubstituted or substituted by a lower alkyl radical, one or two halogen atoms or a trifluoromethyl, nitro or lower alkoxy group; a pyridinyl radical; a piperazinyl radical; a 2-[4-(3-trifluoromethylphenyl)piperazin-1-yl]ethyl radical; a (thiophenyl-2-yl)methyl radical; a (furan-2-yl)methyl radical or a (morpholin-4-yl)ethyl radical;

R$_1$ is hydrogen, a halogen atom, a lower alkyl radical or a group COOR′, in which R′ is hydrogen or a lower alkyl radical; and X is oxygen or sulfur.

According to one embodiment, R is a benzyl radical.

According to another embodiment, R is a methyl radical.

According to another embodiment, R is a phenylethyl radical.

According to another embodiment, X is the oxygen atom.

According to another embodiment, R$_1$ is the hydrogen atom.

According to another embodiment, the nitrogen of the pyridine is in the 4-position. The particularly preferred compounds of the invention are those selected from the products of the formulae

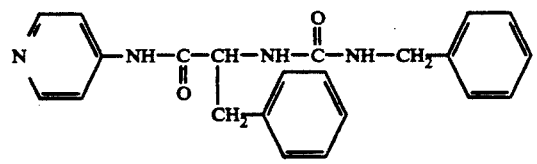

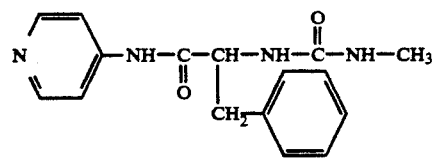

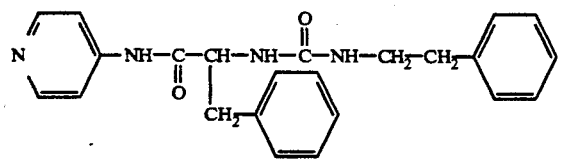

According to the invention, the compounds of formula (I) may be synthesized in the following way:

The reaction of an isocyanate or an isothiocyanate of formula (II):

R—N=C=X in which R and X are as defined above, with a compound of formula (III):

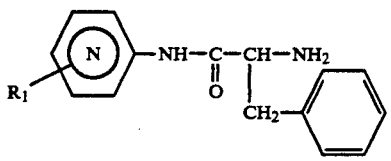

in the (S) configuration, in which $R_1$ is as defined above, in an inert solvent such as tetrahydrofuran, chloroform or methylene chloride, at a temperature of between 20° and 80° C., will yield the compounds of formula (I).

The compounds of formula (II) are commercially available or can be prepared by methods known to those skilled in the art which can be found in the literature, especially under the references:

| | |
|---|---|
| Organic synthesis | vol. II p. 453 |
| Organic synthesis | vol. III p. 599 |

H. Eckert and B. Forster, Angew. Chem. Int. Ed. Engl. 1987, 26, 894

The α-amino-N-pyridylbenzenepropanamides of formula (III) in the (S) configuration are known compounds or are prepared from (L)-phenylalanine as described in the literature under the reference:

J. Altman, M. Gorecki, M. Wilchek, J. R. Voltano and A. Rich: J. Med. Chem. 1984, 27 (5), 596–600

However, the Applicant has found that they can advantageously also be prepared by a method avoiding chromatographic purifications, which are difficult to accept at the industrial stage. This method consists in unblocking the corresponding phthalimide derivatives of formula (IV):

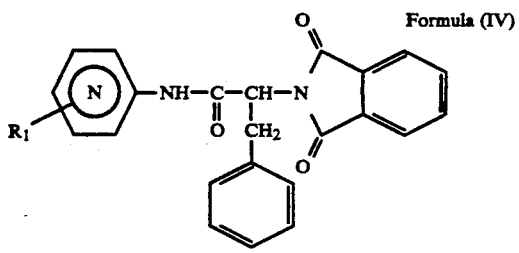

Formula (IV)

in the (S) configuration, in which $R_1$ is as defined above, by reaction with hydrazine hydrate according to the method described in the literature under the reference:

H. R. Ing and R. H. F. Manske: J. Chem. Soc. 1926, 2348.

These α-phthalimido-N-pyridylbenzenepropanamide derivatives of formula (IV) in the (S) configuration were synthesized according to the method described for the pyridin-3-yl and pyridin-4-yl derivatives under the reference:

E. J. Browne and J. B. Polya: J. Chem. Soc. 1968, (23), 2904–8.

Another variant of the preparation of the compounds of formula (I) in which X is the oxygen atom consists in reacting the derivatives of formula (III), in an inert solvent such as tetrahydrofuran, chloroform or methylene chloride, for example at a temperature of between 20° and 80° C., with derivatives of formula (V):

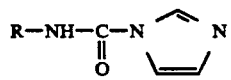

Formula (V)

in which R is as defined above.

The compounds of formula (V) are prepared by reacting carbonyldiimidazole with the corresponding amines R—NH$_2$, in which R is as defined above, according to the method described by:

H. A. Stoab and W. Benz: Annal. Chem. 1961, 72–82.

The compounds of formula (I) as defined above, and their addition salts, in particular pharmaceutically acceptable addition salts, possess a very good analgesic activity.

These properties justify their application in therapy and the invention further relates, by way of drugs, to the products as defined by formula (I) above, and their addition salts, in particular pharmaceutically acceptable addition salts.

Thus the invention also covers a pharmaceutical composition which comprises a pharmaceutically effective amount of at least one compound of formula (I) as defined above, and its pharmaceutically acceptable addition salts if appropriate, which may or may not be incorporated in a pharmaceutically acceptable excipient, vehicle or carrier.

The invention also covers a pharmaceutical composition with analgesic activity affording especially a favorable treatment for pain, which comprises a pharmaceutically effective amount of at least one compound of formula (I) given above, or one of its -pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, and its pharmaceutically acceptable addition salts if appropriate, into a pharmaceutically acceptable excipient, vehicle or carrier. According to another embodiment, a pharmaceutical composition with analgesic activity is prepared which affords especially a favorable treatment for pain.

According to another embodiment, a pharmaceutical composition is formulated as gelatin capsules or tablets containing from 1 mg to 1000 mg of active ingredient, or as injectable preparations containing from 0.1 mg to 500 mg of active ingredient. Formulations as suppositories, ointments, creams, gels or aerosol preparations may also be used.

The invention also covers a method of therapeutic treatment for mammals, which comprises administering to this mammal a therapeutically effective amount of at least one compound of formula (I) as defined above, or one of its pharmaceutically acceptable addition salts. According to an embodiment of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels or aerosol preparations.

In human and animal therapy, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels or aerosol preparations, can be envisaged.

As will be clearly apparent from the pharmacological tests given at the end of the description, the compounds according to the invention can be administered in human therapy for the above-mentioned indications, orally in the form of tablets or gelatin capsules containing from 1 mg to 1000 mg of active ingredient, or parenterally in the form of injectable preparations containing from 0.1 mg to 500 mg of active ingredient, in one or more daily administrations for an adult with an average weight of 60 to 70 kg.

In animal therapy, the daily dose which can be used should normally be between 0.01 and 20 mg per kg.

Other characteristics and advantages of the invention will be understood more clearly from the following description of a few Examples, which in no way imply a limitation but are given by way of illustration.

EXAMPLE 1:

(S)-α-Phthalimido-N-(pyridin-2-yl)benzenepropanamide

Formula (IV): $R_1$=H, pyridin-2-yl 20 g of (S)-α-phthalimidobenzenepropanoyl chloride (prepared according to the reference E. Dorhege, Justus Liebigs Ann. Chem. 1971, 743, 42–49) in 100 ml of anhydrous tetrahydrofuran are added dropwise to a solution of 60 g of 2-aminopyridine in 100 ml of anhydrous tetrahydrofuran, in the presence of one equivalent of triethylamine. The mixture is then refluxed for 5 hours, after which the tetrahydrofuran is evaporated off under vacuum. The brown oil obtained is taken up with chloroform and the solution is washed with water, dried and then evaporated. The residue thus obtained crystallizes from ethanol. The crystals are filtered off, washed with a small amount of ethanol and dried. 22 g of (S)-α-phthalimido-N-(pyridin-2-yl)benzenepropanamide are recovered in the form of a beige solid melting at 178° C.

EXAMPLE 2:

(S)-α-Phthalimido-N-(5-carboxyethylpyridin-3-yl)benzenepropanamide

Formula (IV): $R_1$=5—$COOC_2H_5$, pyridin-3-yl

Prepared according to the procedure of Example 1 using ethyl 5-aminonicotinate. Yield 90%; melting point 201° C.

EXAMPLE 3:

(S)-α-Amino-N-(5-carboxyethylpyridin-3-yl)benzenepropanamide

Formula (III): $R_1$=5—$COOC_2H_5$, pyridin-3-yl

A solution of 33.4 g of (S)-α-phthalimido-N-(5-carboxyethylpyridin-3-yl)benzenepropanamide, prepared in Example 2, in ethanol is refluxed for 5 hours in the presence of 3.7 ml of hydrazine hydrate. The ethanol is then evaporated off under vacuum, the residue is treated with dilute hydrochloric acid of pH 1 and the solution obtained is filtered. The filtrate is then rendered basic in the cold with a solution of sodium hydroxide and subsequently extracted with methylene chloride. The organic phase is washed with water and dried and the solvent is evaporated off to give 11.7 g of a brown oil, which is used as such for the next step.

EXAMPLE 4:

N-(4-Methoxybenzyl)imidazole-1-carboxamide

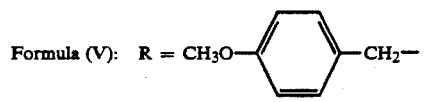

Formula (V): R = $CH_3O$—⟨phenyl⟩—$CH_2$—

23.6 g of carbonyldiimidazole are added in portions to a solution of 20 g of 4-methoxybenzylamine in 100 ml of anhydrous tetrahydrofuran, the temperature being kept below 10° C. When the addition is complete, the mixture is allowed to return to room temperature and stirring is maintained for three hours. After filtration, the tetrahydrofuran phase is evaporated under vacuum and the residue obtained is taken up with methylene chloride, washed with water and then dried. The oil obtained after evaporation of the methylene chloride is crystallized from ether. The crystals obtained are filtered off and then dried. 22.7 g of N-(4-methoxybenzyl)imidazolecarboxamide are thus recovered in the form of crystals melting at 117° C.

The products of Examples 5 to 16 were obtained according to this procedure:

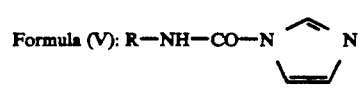

Formula (V): R—NH—CO—N⟨imidazole⟩

| Example | R | Melting point | Yield |
| --- | --- | --- | --- |
| 5 | p-fluorobenzyl | 102° C. | 57% |
| 6 | p-chlorobenzyl | 86° C. | 58% |
| 7 | p-methylbenzyl | 129° C. | 70% |
| 8 | pyridin-4-ylmethyl | 114° C. | 33% |
| 9 | o-fluorobenzyl | 107° C. | 57% |
| 10 | pyridin-3-ylmethyl | 116° C. | 39% |
| 11 | 2,6-difluorobenzyl | 138° C. | 48% |
| 12 | cyclohexylmethyl | 96° C. | 53% |
| 13 | o-methylbenzyl | 85° C. | 60% |
| 14 | p-nitrobenzyl | 162° C. | 85% |
| 15 | 3-phenylpropyl | 68° C. | 57% |

-continued

Formula (V): R—NH—CO—N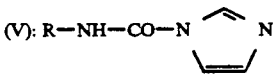N

| Example | R | Melting point | Yield |
|---|---|---|---|
| 16 | 2-[4-(3-trifluoro-methylphenyl)piperazin-1-yl]ethyl | 83° C. | 45% |

EXAMPLE 17:

(S)-N'-Benzyl-N''-[N-(pyridin-4-yl)benzenepropana-mid-2-yl]urea

Formula (I): R=benzyl, X=O, $R_1$=H, pyridin-4-yl

A solution of 3 g of (S)-α-amino-N-(pyridin-4-yl)-benzenepropanamide and 1.17 g of benzyl isocyanate in 50 ml of methylene chloride is stirred at room temperature for 8 h. The precipitate formed is filtered off, washed with methylene chloride and then dried to give 3.6 g of (S)-N'-benzyl-N''-[N-(pyridin-4-yl)-benzenepropana-mid-2-yl]urea in the form of crystals melting at 178° C., the IR, NMR and CHN analysis of which are consistent with those of the pure product.

The compounds of Examples 18 to 46 in the (S) configuration are obtained according to an identical method by reacting the corresponding (S)-α-amino-N-pyridylbenzenepropanamides either with isocyanates or isothiocyanates which are commercially available or prepared according to the references cited, or with the imidazole-1-carboxamide derivatives of Examples 4 to 16.

EXAMPLE 18:

(S)-N'-Benzyl-N''-[N-(pyridin-4-yl)benzenepropana-mid-2-yl]thiourea

Formula (I): R=benzyl, X=S, $R_1$=H, pyridin-4-yl

Crystals melting at 122° C.
Yield 34%

| Analysis: $C_{22}H_{22}N_4OS$ MW: 390.5 | | | |
|---|---|---|---|
| Calculated | C % 67.66 | H % 5.68 | N % 14.35 |
| Found | 67.4 | 5.70 | 14.20 |

EXAMPLE 19:

(S)-N'-Methyl-N''-[N-(pyridin-4-yl)benzenepropana-mid-2-yl]thiourea

Formula (I): R=methyl, X=S, $R_1$=H, pyridin-4-yl

Crystals melting at 113° C.
Yield 26%

| Analysis: $C_{16}H_{18}N_4OS$ MW = 314.4 | | | |
|---|---|---|---|
| Calculated | C % 61.12 | H % 5.77 | N % 17.82 |
| Found | 61.0 | 5.88 | 17.72 |

EXAMPLE 20:

(S)-N'-Phenyl-N''-[N-(pyridin-4-yl)benzenepropana-mid-2-yl]thiourea

Formula (I): R=phenyl, X=S, $R_1$=H, pyridin-4-yl

Crystals melting at 138° C.
Yield 45%

| Analysis: $C_{21}H_{20}N_4OS$ MW = 376.47 | | | |
|---|---|---|---|
| Calculated | C % 66.99 | H % 5.36 | N % 14.88 |
| Found | 66.8 | 5.24 | 14.83 |

EXAMPLE 21:

(S)-N'-t-Butyl-N''-[N-(pyridin-4-yl)benzenepropana-mid-2-yl]thiourea

Formula (I): R=t-butyl, X=S, $R_1$=H, pyridin-4-yl

Crystals melting at 167° C.
Yield 48%

| Analysis: $C_{19}H_{24}N_4OS$ MW = 356.5 | | | |
|---|---|---|---|
| Calculated | C % 64.0 | H % 6.79 | N % 15.72 |
| Found | 63.7 | 6.84 | 15.74 |

EXAMPLE 22:

(S)-N'-(2-Phenylethyl)-N''-[N-(pyridin-4-yl)benzene-propanamid-2-yl]thiourea

Formula (I): R=2-phenylethyl, X=S, $R_1$=H, pyridin-4-yl

Crystals melting at 117° C.
Yield 32%

| Analysis: $C_{23}H_{24}N_4OS$ MW = 404.5 | | | |
|---|---|---|---|
| Calculated | C % 68.3 | H % 5.98 | N % 13.85 |
| Found | 68.5 | 5.94 | 13.98 |

EXAMPLE 23:

(S)-N'-Phenyl-N''-[N-(pyridin-4-yl)benzenepropana-mid-2-yl]urea

Formula (I): R=phenyl, X=O, $R_1$=H, pyridin-4-yl

Crystals melting at 163
Yield 30%

| Analysis: $C_{21}H_{20}N_4O_2$ MW = 360.4 | | | |
|---|---|---|---|
| Calculated | C % 70.0 | H % 5.59 | N % 15.5 |
| Found | 69.9 | 5.57 | 15.63 |

EXAMPLE 24:

(S)-N'-(2-Phenylethyl)-N''-[N-(pyridin-4-yl)benzen-propanamid-2-yl]urea

Formula (I): R=2-phenylethyl, X=O, $R_1$=H, pyridin-4-yl

Crystals melting at 158° C.
Yield 33%

| Analysis: $C_{23}H_{24}N_4O_2$ MW = 388.4 | | | |
|---|---|---|---|
| Calculated | C % 71.1 | H % 6.23 | N % 14.42 |
| Found | 70.8 | 6.10 | 14.17 |

EXAMPLE 25:

(S)-N'-t-Butyl-N''-[N-(pyridin-4-yl)benzenepropanamid-2-yl]urea

Formula (I): R=t-butyl, X=O, R₁=H, pyridin-4-yl

Crystals melting at 203° C.
Yield 39%

| Analysis: C₁₈H₂₄N₄O MW = 312.4 | | | |
|---|---|---|---|
| Calculated | C % 67.0 | H % 7.10 | N % 16.46 |
| Found | 66.7 | 7.03 | 16.47 |

EXAMPLE 26:

(S)-N'-[(S)-1-Phenylethyl]-N''-[N-pyridin-4-yl)benzenepropanamid-2-yl]urea

Formula (I): R=(S)-1-phenylethyl, X=O, R₁=H, pyridin-4-yl, R₄=phenyl

Crystals melting at 159° C.
Yield 40%

| Analysis: C₂₃H₂₄N₄O₂ MW = 388.4 | | | |
|---|---|---|---|
| Calculated | C % 71.1 | H % 6.23 | N % 14.42 |
| Found | 71.1 | 6.26 | 14.49 |

EXAMPLE 27:

(S)-N'-[(R)-1-Phenylethyl]-N''-[N-(pyridin-4-yl)benzenepropanamid-2-yl]urea

Formula (I): R=(R)-1-phenylethyl, X=O, R₁=H, pyridin-4-yl

Crystals melting at 169° C.
Yield 74%

| Analysis: C₂₃H₂₄N₄O₂ MW = 388.4 | | | |
|---|---|---|---|
| Calculated | C % 71.1 | H % 6.23 | N % 14.42 |
| Found | 71.1 | 6.24 | 14.42 |

EXAMPLE 28:

(S)-N'-(4-Fluorobenzyl)-N''-[N-(pyridin-4-yl)benzenepropanamid-2-yl]urea

Formula (I): R=4-fluorobenzyl, X=O, R₁=H, pyridin-4-yl

Crystals melting at 197° C.
Yield 44%

| Analysis: C₂₂H₂₁FN₄O₂ MW = 392.4 | | | |
|---|---|---|---|
| Calculated | C % 67.3 | H % 5.39 | N % 14.38 |
| Found | 67.1 | 5.32 | 14.32 |

EXAMPLE 29:

(S)-N'-(4-Chlorobenzyl)-N''-[N-(pyridin-4-yl)benzenepropanamid-2-yl]urea

Formula (I): R=4-chlorobenzyl, X=O, R₁=H, pyridin-4-yl

Crystals melting at 197° C.
Yield 42%

| Analysis: C₂₂H₂₁ClN₄O₂ MW = 408.9 | | | |
|---|---|---|---|
| Calculated | C % 64.6 | H % 5.18 | N % 13.70 |
| Found | 64.2 | 5.03 | 13.54 |

EXAMPLE 30:

(S)-N'-(4-Trifluoromethylbenzyl)-N''-[N-(pyridin-4-yl)benzenepropanamid-2-yl]urea Formula (I): R=4-trifluoromethylbenzyl, X=O, R₁=H, pyridin-4-yl Crystals melting at 198° C.
Yield 86%

| Analysis: C₂₃H₂₁F₃N₄O₂ MW = 442.4 | | | |
|---|---|---|---|
| Calculated | C % 62.4 | H % 4.78 | N % 12.66 |
| Found | 62.4 | 4.72 | 12.71 |

EXAMPLE 31:

(S)-N'-(4-Methoxybenzyl)-N''-[N-(pyridin-4-yl)benzenepropanamid-2-yl]urea

Formula (I): R=4-methoxybenzyl, X=O, R₁=H, pyridin-4-yl

Crystals melting at 184° C.
Yield 54%

| Analysis: C₂₃H₂₄N₄O₃ MW = 404.4 | | | |
|---|---|---|---|
| Calculated | C % 68.3 | H % 5.98 | N % 13.85 |
| Found | 68.1 | 5.89 | 13.75 |

EXAMPLE 32:

(S)-N'-(4-Methylbenzyl)-N''-[N-(pyridin-4-yl)benzenepropanamid-2-yl]urea

Formula (I): R=4-methylbenzyl, X=O, R₁=H, pyridin-4-yl

Crystals melting at 192° C.
Yield 48%

| Analysis: C₂₃H₂₄N₄O₂ MW = 388.4 | | | |
|---|---|---|---|
| Calculated | C % 71.1 | H % 6.23 | N % 14.42 |
| Found | 70.8 | 6.02 | 14.40 |

EXAMPLE 33:

(S)-N'-(Pyridin-4-ylmethyl)-N''-[N-(pyridin-4-yl)benzenepropanamid-2-yl]urea

Formula (I): R=pyridin-4-ylmethyl, X=O, R₁=H, pyridin-4-yl

Crystals melting at 191° C.
Yield 46%

| Analysis: C₂₁H₂₁N₅O₂ MW = 375.4 | | | |
|---|---|---|---|
| Calculated | C % 67.2 | H % 5.64 | N % 18.66 |
| Found | 67.4 | 5.70 | 18.97 |

EXAMPLE 34:

(S)-N'-(2-Fluorobenzyl)-N''-[N-(pyridin-4yl)benzene-propanamid-2-yl]urea

Formula (I): R=2-fluorobenzyl, X=O, $R_1$=H, pyridin-4-yl

Crystals melting at 199° C.
Yield 22%

| Analysis: $C_{22}H_{21}FN_4O_2$ MW = 392.4 | | | |
|---|---|---|---|
| Calculated | C % 67.3 | H % 5.39 | N % 14.28 |
| Found | 67.4 | 5.33 | 14.28 |

EXAMPLE 35:

(S)-N'-Benzyl-N''-[N-(pyridin-3-yl)benzenepropanamid-2-yl]urea

Formula (I): R=benzyl, X=O, $R_1$=H, pyridin-3-yl

Crystals melting at 172° C.
Yield 84%

| Analysis: $C_{22}H_{22}N_4O_2$ MW = 374.4 | | | |
|---|---|---|---|
| Calculated | C % 70.6 | H % 5.92 | N % 14.96 |
| Found | 70.5 | 5.94 | 15.07 |

EXAMPLE 36:

(S)-N'-(3-Trifluoromethylbenzyl)-N''-[N-((pyridin-4-yl)benzenepropanamid-2-yl]urea Formula (I): R=3-trifluoromethylbenzyl, X=O, $R_1$=H, pyridin-4-yl Crystals melting at 173° C.
Yield 55%

| Analysis: $C_{23}H_{21}F_3N_4O_2$ MW = 442.4 | | | |
|---|---|---|---|
| Calculated | C % 62.4 | H % 4.78 | N % 12.66 |
| Found | 62.4 | 4.75 | 12.74 |

EXAMPLE 37:

(S)-N'-Benzyl-N''-[N-(5-carboxyethylpyridin-3-yl)benzenepropanamid-2-yl]urea

Formula (I): R=benzyl, X=O, $R_1$=5-$CO_2$Et, pyridin-3-yl

Crystals melting at 198° C.
Yield 75%

| Analysis: $C_{25}H_{26}N_4O_4$ MW = 446.5 | | | |
|---|---|---|---|
| Calculated | C % 67.2 | H % 5.87 | N % 12.55 |
| Found | 66.8 | 5.81 | 12.53 |

EXAMPLE 38:

(S)-N'-Benzyl-N''-[N-(pyridin-2-yl)benzenepropanamid-2 yl]urea

Formula (I): R=benzyl, X=O, $R_1$=H, pyridin-2-yl

Crystals melting at 156° C.
Yield 78%

| Analysis: $C_{22}H_{22}N_4O_2$ MW = 374.4 | | | |
|---|---|---|---|
| Calculated | C % 70.6 | H % 5.92 | N % 14.96 |
| Found | 70.5 | 5.80 | 15.09 |

EXAMPLE 39:

(S)-N'-(Pyridin-2-ylmethyl)-N''-[N-(pyridin-4-yl)benzenepropanamid-2-yl]urea

Formula (I): R=pyridin-2-ylmethyl, X=O, $R_1$=H, pyridin-4-yl

Crystals melting at 159° C.
Yield 25%

| Analysis: $C_{21}H_{21}N_5O_2$ MW = 375.4 | | | |
|---|---|---|---|
| Calculated | C % 67.2 | H % 5.64 | N % 18.66 |
| Found | 67.1 | 5.70 | 18.39 |

EXAMPLE 40:

(S)-N'-(2,6-Difluorobenzyl)-N''-[N-(pyridin-4-yl)benzenepropanamid-2-yl]urea

Formula (I): R=2,6-difluorobenzyl, X=O, $R_1$=H, pyridin-4-yl

Crystals melting at 184° C.
Yield 30%

| Analysis: $C_{22}H_{20}F_2N_4O_2$ MW = 410.4 | | | |
|---|---|---|---|
| Calculated | C % 64.4 | H % 4.91 | N % 13.65 |
| Found | 64.2 | 4.79 | 13.67 |

EXAMPLE 41:

(S)-N'-Methyl-N''-[N-(pyridin-4-yl)benzenepropanamid-2-yl]urea

Formula (I): R=methyl, X=O, $R_1$=H, pyridin-4-yl

Crystals melting at 171° C.
Yield 32%

| Analysis: $C_{16}H_{18}N_4O_2$ MW = 298.3 | | | |
|---|---|---|---|
| Calculated | C % 64.4 | H % 6.08 | N % 18.78 |
| Found | 64.3 | 6.17 | 18.80 |

EXAMPLE 42:

(S)-N'-(3-Phenylprop-1-yl)-N''-[N-(pyridin-4-yl)benzenepropanamid-2-yl]urea

Formula (I): R=3-phenylprop-1-yl, X=O, $R_1$=H, pyridin-4-yl

Crystals melting at 178° C.
Yield 27%

| Analysis: $C_{24}H_{26}N_4O_2$ MW = 402.5 | | | |
|---|---|---|---|
| Calculated | C % 71.6 | H % 6.51 | N % 13.92 |
| Found | 71.8 | 6.60 | 14.18 |

EXAMPLE 43:

(S)-N'-(2-Methylbenzyl)-N"-[N-(pyridin-4-yl)benzene-propanamid-2-yl]urea

Formula (I): R=2-methylbenzyl, X=O, R₁=H, pyridin-4-yl

Crystals melting at 182° C.
Yield 36%

| Analysis: $C_{23}H_{24}N_4O_2$ MW = 388.45 | | | |
|---|---|---|---|
| Calculated | C % 71.1 | H % 6.23 | N % 14.42 |
| Found | 71.2 | 6.30 | 14.54 |

EXAMPLE 44:

(S)-N'-Cyclohexylmethyl-N"-[N-(pyridin-4-yl)ben-zenepropanamid-2-yl]urea

Formula (I): R=cyclohexylmethyl, X=O, R₁=H, pyridin-4-yl

Crystals melting at 205° C.
Yield 23%

| Analysis: $C_{22}H_{28}N_4O_2$ MW = 380.5 | | | |
|---|---|---|---|
| Calculated | C % 69.4 | H % 7.42 | N % 14.73 |
| Found | 69.5 | 7.53 | 14.92 |

EXAMPLE 45:

(S)-N'-(4-Nitrobenzyl)-N"-[N-(pyridin-4-yl)benzene-propanamid-2-yl]urea

Formula (I): R=4-nitrobenzyl, X=O, R₁=H, pyridin-4-yl

Crystals melting at 207° C.
Yield 41%

| Analysis: $C_{22}H_{21}N_5O_4$ MW = 419.4 | | | |
|---|---|---|---|
| Calculated | C % 63.0 | H % 5.05 | N % 16.70 |
| Found | 62.9 | 5.00 | 16.69 |

EXAMPLE 46:

(S)-N'-[2-[4-(3-Trifluoromethylphenyl)piperazin-1-yl]e-thyl]-N"-[N-(pyridin-4-yl)benzenepropanamid-2-yl]urea Formula (I):
R=2-[4-(3-trifluoromethylphenyl)piperazin-1-yl]ethyl, X=O, R₁=H, pyridin-4-yl Crystals melting at 174° C.
Yield 20%

| Analysis: $C_{28}H_{31}F_3N_6O_2$ MW = 540.6 | | | |
|---|---|---|---|
| Calculated | C % 62.2 | H % 5.78 | N % 15.55 |
| Found | 62.1 | 5.71 | 15.41 |

The intermediates of Examples 47 to 54 were also obtained from commercially available amines by the method described in Example 4.

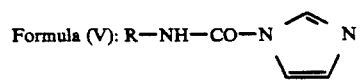

Formula (V): R—NH—CO—N⌒N

| Example | R | Melting point | Yield |
|---|---|---|---|
| 47 | n-undecyl | 59° C. | 70% |
| 48 | (2-thienyl)methyl | 126° C. | 83% |
| 49 | 2-furfuryl | 131° C. | 60% |
| 50 | 3-methylbenzyl | 97° C. | 68% |
| 51 | 2-methylprop-1-yl | oil | 64% |
| 52 | 1-ethylprop-1-yl | oil | 67% |
| 53 | 3-methylbut-1-yl | oil | 80% |
| 54 | (morpholin-4-yl)ethyl | oil | 65% |

The products of Examples 55 to 66 were obtained by reacting the products 47 to 54 or commercially available isocyanates with (S)-α-amino-N-(pyridin-4-yl)benzenepropanamide by the procedure described in Example 17.

EXAMPLE 55:

(S)-N'-(n-Undecyl)-N"-[N-(pyridin-4-yl)benzene-propanamid-2-yl]urea

Formula (I): R=n-undecyl, X=O, R₁=H, pyridin-4-yl

Crystals melting at 124° C.
Yield 46%

| Analysis: $C_{27}H_{40}N_4O_2$ MW = 452.6 | | | |
|---|---|---|---|
| Calculated | C % 71.6 | H % 8.91 | N % 12.4 |
| Found | 71.7 | 9.00 | 12.6 |

EXAMPLE 56:

(S)-N'-(2-Thienyl-2-yl)methyl-N"-[N-(pyridin-4-yl)benezenepropanamid-2-yl]urea

Formula (I): R=(2-thienyl)methyl, X=O, R₁=H, pyridin-4-yl

Crystals melting at 196° C.
Yield 57%

| Analysis: $C_{20}H_{20}N_4O_2S$ MW = 381.46 | | | |
|---|---|---|---|
| Calculated | C % 62.97 | H % 5.55 | N % 14.69 |
| Found | 62.7 | 5.33 | 14.40 |

EXAMPLE 57:

(S(-N'-(2-furfuryl)-N"-[N-pyridin-4-yl)benzene-propanamid-2-yl]urea

Formula (I): R=2-furfuryl, X=O, R₁=H, pyridin-4-yl

Crystals melting at 220° C.
Yield 47%

| Analysis: $C_{20}H_{20}N_4O_3$ MW = 364.40 | | | |
|---|---|---|---|
| Calculated | C % 65.9 | H % 5.53 | N % 15.4 |
| Found | 65.9 | 5.53 | 15.3 |

EXAMPLE 58:

(S)-N'-(3-Methylbenzyl)-N'''-[N-(pyridin-4-yl)benzene-propanamid-2-yl]urea

Formula (I): R=3-methylbenzyl, X=O, R₁=H, pyridin-4-yl

Crystals melting at 195° C.
Yield 35%

| Analysis: C₂₃H₂₄N₄O₂ MW = 388.47 | | | |
|---|---|---|---|
| Calculated | C % 71.1 | H % 6.23 | N % 14.42 |
| Found | 71.0 | 6.35 | 14.3 |

EXAMPLE 59:

(S)-N'-(2-Methylprop-1-yl)-N'''-[N-(pyridin-4-yl)benzenepropanamid-2-yl]urea

Formula (I): R=2-methylprop-1-yl, X=O, R₁=H, pyridin-4-yl

Crystals melting at 176° C.
Yield 32%

| Analysis: C₁₉H₂₄N₄O₂ MW = 340.41 | | | |
|---|---|---|---|
| Calculated | C % 67.03 | H % 7.11 | N % 16.46 |
| Found | 66.6 | 7.30 | 16.1 |

EXAMPLE 60:

(S)-N'-(1-Ethylprop-1-yl)-N'''-[N-(pyridin-4-yl)benzenepropanamid-2-yl]urea

Formula (I): R=1-ethylprop-1-yl, X=O, R₁=H, pyridin-4-yl

Crystals melting at 203° C.
Yield 60%

| Analysis: C₂₀H₂₆N₄O₂ MW = 354.4 | | | |
|---|---|---|---|
| Calculated | C % 67.77 | H % 7.39 | N % 15.8 |
| Found | 67.6 | 7.35 | 15.8 |

EXAMPLE 61:

(S)-N'-(3-Methylbut-1-yl)-N'''-[N-(pyridin-4yl)benzenepropanamid-2-yl]urea

Formula (I): R=3-methylbut-1-yl, X=O, R₁=H, pyridin-4-yl

Crystals melting at 174° C.
Yield 3%

| Analysis: C₂₀H₂₆N₄O₂ MW = 354.4 | | | |
|---|---|---|---|
| Calculated | C % 67.77 | H % 7.39 | N % 15.8 |
| Found | 67.8 | 7.41 | 15.7 |

EXAMPLE 62:

(S)-N'-(Morpholin-4-ylethyl)-N'''-[N-(pyridin-4-yl)benzenepropanamid-2-yl]urea

Formula (I): R=morpholin-4-ylethyl, X=O, R₁=H, pyridin-4-yl

Crystals melting at 163° C.
Yield 11%

| Analysis: C₂₁H₂₇N₅O₃ MW = 397.5 | | | |
|---|---|---|---|
| Calculated | C % 63.5 | H % 6.85 | N % 17.62 |
| Found | 63.2 | 6.93 | 17.5 |

EXAMPLE 63:

(S)-N'-(n-Propyl)-N'''-[N-(pyridin-4-yl)benzenepropanamid-2-yl]urea

Formula (I): R=n-propyl, X=O, R₁=H, pyridin-4-yl

Crystals melting at 172° C.
Yield 33%

| Analysis: C₁₈H₂₂N₄O₂ MW = 326.4 | | | |
|---|---|---|---|
| Calculated | C % 66.2 | H % 6.80 | N % 17.2 |
| Found | 66.1 | 6.86 | 17.1 |

EXAMPLE 64:

(S)-N'-(n-Butyl)-N'''-[N-(pyridin-4-yl)benzenepropanamid-2-yl]urea

Formula (I): R=n-butyl, X=O, R₁=H, pyridin-4-yl

Crystals melting at 155° C.
Yield 51%

| Analysis: C₁₉H₂₄N₄O₂ MW = 340.4 | | | |
|---|---|---|---|
| Calculated | C % 67.0 | H % 7.11 | N % 16.46 |
| Found | 67.1 | 7.16 | 16.6 |

EXAMPLE 65:

(S)-N'-(1-Methylethyl)-N'''-[N-(pyridin-4-yl)benzene-propanamid-2-yl]urea

Formula (I): R=1-methylethyl, X=O, R₁=H, pyridin-4-yl

Crystals melting at 182° C.
Yield 30%

| Analysis: C₁₈H₂₂N₄O₂ MW = 326.39 | | | |
|---|---|---|---|
| Calculated | C % 66.23 | H % 6.79 | N % 17.2 |
| Found | 66.2 | 6.86 | 17.2 |

EXAMPLE 66:

(S)-[N-(Pyridin-4-yl)benzenepropanamid-2-yl]urea

Formula (I): R=H, X=O, R₁=H, pyridin-4-yl

Crystals melting at 157° C.
Yield 28%

| Analysis: C₁₅H₁₆N₄O₂ MW = 284.3 | | | |
|---|---|---|---|
| Calculated | C % 63.37 | H % 5.17 | N % 19.7 |
| Found | 63.2 | 5.30 | 19.5 |

PHARMACOLOGY

The analgesic activity of the products of the Examples was evaluated according to the method involving the stretching movements caused by phenylbenzoquinone in mice, described by Siegmund et al. (1957).

METHOD

The intraperitoneal injection of phenylbenzoquinone causes twisting and stretching movements in mice. Analgesics prevent or reduce this syndrome, which can be considered as the exteriorization of a diffuse abdominal pain.

A 0.02% solution of phenylbenzoquinone in water is administered in a volume of 1 ml/100 g.

The products of the Examples are administered orally one hour before the injection of phenylbenzoquinone.

The stretching and twisting movements are counted for each mouse over an observation period of 5 minutes.

Expression of the Results

The results are expressed in the form of the $ID_{50}$, i.e. the dose which affords a 50% reduction in the number of pain reactions compared with the control animals.

Results

The results are presented in the Table below.

| Product of | 50% inhibitory dose mg/kg p.o. |
|---|---|
| Example 17 | 3.0 (2.3–3.9) |
| Example 20 | 32.3 (26.0–40.0) |
| Example 21 | 20.3 (12.9–32.1) |
| Example 22 | 12.3 (7.0–21.4) |
| Example 23 | 8.9 (7.3–11.0) |
| Example 41 | ~9 |

TOXICOLOGY

The first toxicology studies performed show that the majority of the products of the Examples do not induce any deleterious effects in rats after the oral absorption of doses which can vary from 30 to 300 mg/kg.

What is claimed is:

1. An α-amino-N-pyridylbenzenepropanamide compound of the formula:

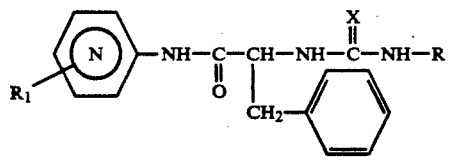

and having the (S) configuration, wherein:
   the amide substituent on the pyridine ring is ortho, meta or para to the nitrogen in the pyridine ring;
   R is hydrogen or —(CH—R$_4$)$_n$—A wherein R$_4$ is selected from the group consisting of hydrogen; phenyl; and phenyl substituted by lower alkyl, one or two halogens, trifluoromethyl, nitro, amino, hydroxy, lower alkoxy, thiol or lower alkyl thio; n is an integer from 0 to 5;
   A is selected from the group consisting of lower alkyl; $C_3$-$C_7$ cycloalkyl; phenyl, furanyl, thienyl or pyridyl, substituted by lower alkyl, one or two halogens, trifluoromethyl, nitro, amino, hydroxy, lower alkoxy, thiol or lower alkyl thio; or —(CH$_2$)$_n$—N(R$_2$R$_3$) in which n is as defined above and R$_2$ and R$_3$ are identical or different and are lower alkyl, $C_3$-$C_7$ cycloalkyl or form, together with the nitrogen atom to which they are attached, a ring selected from the group consisting of morpholine and piperazine N-substituted by lower alkyl, $C_3$-$C_7$ cycloalkyl, phenyl and phenyl substituted by lower alkyl, one or two halogens, trifluoromethyl, nitro, amino, hydroxy, lower alkoxy, thiol or thio lower alkyl;
   R$_1$ is selected from the group consisting of hydrogen, halogen, lower alkyl and COOR' wherein R' is hydrogen or lower alkyl; and
   x is oxygen or sulfur;
   or a pharmacologically acceptable salt thereof.

2. An α-amino-N-pyridylbenzenepropanamide compound of the formula:

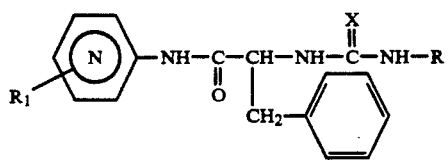

and having the (S) configuration wherein
   the amide substituent on the pyridine ring is ortho, meta or para to the nitrogen in the pyridine ring;
   R is hydrogen; phenethyl; —(CH$_2$)$_n$—A, wherein n is an integer from 0 to 5 and A is selected from the group consisting of lower alkyl, $C_3$-$C_7$ cycloalkyl, phenyl, phenyl substituted by lower alkyl, one or two halogens, trifluoromethyl, nitro, and lower alkoxy; pyridinyl; piperazzinyl; 2-[4-(3-trifluoromethylphenyl)piperazinyl-1-yl ]ethyl; (2-thienyl)methyl; 2-furfuryl and; (morpholin-4-yl)ethyl;
   R$_1$ is hydrogen; halogen; lower alkyl; or COOR', wherein R' is hydrogen or lower alkyl; and
   X is oxygen or sulfur;
   or a pharmacologically acceptable salt thereof.

3. A compound according to claim 1 or claim 2, wherein R is benzyl.

4. A compound according to claim 1 or claim 2, wherein R is methyl.

5. A compound according to claim 1 or claim 2, wherein R is phenethyl.

6. A compound according to claim 1 or claim 2, wherein X is oxygen.

7. A compound according to claim 1 or claim 2, wherein R$_1$ is hydrogen.

8. A compound according to claim 1 or claim 2, wherein the amide substituent on the pyridine ring is para to the nitrogen in the pyridine ring.

9. A compound according to claim 1 or claim 2, which is

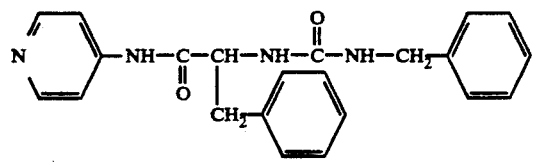

-continued

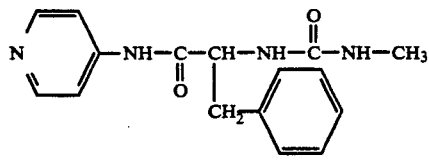

or

-continued

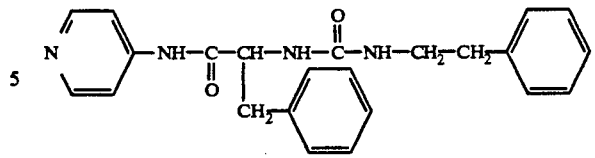

10. An analgesic composition comprising an analgesically effective amount of a compound as defined in claim 1 or claim 2 incorporated in a pharamaceutically acceptable excipient, vehicle or carrier.

11. An analgesic composition formulated as gelatine capsules or tablets containing from 1 mg to 1000 mg of a compound as defined in claim 1 or claim 2 incorporated in a pharmaceutically acceptable excipient, vehicle or carrier.

12. An analgesic injectable composition containing from 0,1 to 500 mg of a compound as defined in claim 1 or claim 2, incorporated in a pharmaceutically acceptable excipient, vehicle or carrier.

* * * * *